(12) United States Patent
Cullen et al.

(10) Patent No.: US 9,675,728 B2
(45) Date of Patent: *Jun. 13, 2017

(54) COMPOSITIONS FOR WOUND TREATMENT

(75) Inventors: Breda Mary Cullen, Skipton (GB);
Derek Walter Silcock, Skipton (GB)

(73) Assignee: KCI USA, Inc., San Antonio, TX (US)

( * ) Notice: Subject to any disclaimer, the term of this patent is extended or adjusted under 35 U.S.C. 154(b) by 2102 days.

This patent is subject to a terminal disclaimer.

(21) Appl. No.: 10/528,262

(22) PCT Filed: Sep. 17, 2003

(86) PCT No.: PCT/GB03/04019
§ 371 (c)(1),
(2), (4) Date: Nov. 18, 2005

(87) PCT Pub. No.: WO2004/026200
PCT Pub. Date: Apr. 1, 2004

(65) Prior Publication Data
US 2006/0172000 A1 Aug. 3, 2006

(30) Foreign Application Priority Data
Sep. 18, 2002 (GB) .................................. 0221688.5

(51) Int. Cl.
A61L 15/00 (2006.01)
A61L 15/22 (2006.01)
A61L 15/44 (2006.01)

(52) U.S. Cl.
CPC ............. *A61L 15/225* (2013.01); *A61L 15/44* (2013.01)

(58) Field of Classification Search
USPC ...................................................... 424/445
See application file for complete search history.

(56) References Cited

U.S. PATENT DOCUMENTS

| 2,157,224 | A |   | 5/1939  | Wagner et al. |        |
|-----------|---|---|---------|---------------|--------|
| 2,517,772 | A |   | 8/1950  | Doub et al.   |        |
| 3,122,479 | A |   | 2/1964  | Smith         |        |
| 3,157,524 | A |   | 11/1964 | Artandi       |        |
| 5,770,228 | A | * | 6/1998  | Edwards       | A61K 9/0014 |
|           |   |   |         |               | 424/488 |
| 5,836,970 | A | * | 11/1998 | Pandit        | 606/213 |
| 6,201,164 | B1|   | 3/2001  | Wulff et al.  |        |
| 7,252,837 | B2| * | 8/2007  | Guo et al.    | 424/443 |

FOREIGN PATENT DOCUMENTS

| EP | 0393825 A1 | 10/1990 | |
| EP | 0437095 A  | 12/1990 | |
| EP | 0541391 A1 | 5/1993  | |
| EP | 0562862 A1 | 9/1993  | |
| EP | 0794223 B  | 9/2003  | |
| EP | 1 378 255 A | 1/2004 | |
| FR | 2736835 A  | 7/1995  | |
| GB | 1280631    | 7/1972  | |
| GB | 2314865 A  | 1/1998  | |
| GB | WO 00/33893 | * 6/2000 | |
| JP | 5-305129 A | 11/1993 | |
| JP | 10-151184 A | 6/1998 | |
| WO | WO 98/00180 | 1/1998 | |
| WO | WO9800446  | * 1/1998 | ............. A61K 47/36 |
| WO | WO 99/01166 A | 1/1999 | |

OTHER PUBLICATIONS

Liu et al. (Chitosan coated cotton fiber: preparation and physical properties, Carbohydrate polymer, 2001, vol. 44, pp. 233-238).*
Antoniades, Human platelet-derived growth factor (PDGF): Purification of PDGF-I and PDGF-II and separation of their reduced sub units, 78 Proc. Natl. Acad. Sci. USA 7314 (1981).
Product Information Sheet for PDGFR, beta, sold by Thermo Scienthc. downloaded Jul. 22, 2016.
Product Information Sheet for hPDGF-BB, sold by Cell Signaling Technology. Rev. Mar. 9, 2016.
Reigstad, et al., Platelet-derived Growth Factor (PDGF)-C, a PDGF Family Member with a Vascular Endothelial Growth Factor-like Structure, 278 J. Biological Chemistry 17114 (2003).

* cited by examiner

*Primary Examiner* — Bethany Barham
*Assistant Examiner* — Ping Cao
(74) *Attorney, Agent, or Firm* — Harness, Dickey & Pierce, P.L.C.

(57) ABSTRACT

A wound dressing composition comprising a chitosan and an oxidized cellulose. For example, the composition may be in the form of a sponge formed by freeze drying an aqueous dispersion of chitosan and oxidized regenerated cellulose (ORC). The composition is especially suitable for the treatment of chronic wounds.

10 Claims, 2 Drawing Sheets

COMPOSITIONS FOR WOUND TREATMENT

CROSS-REFERENCE TO RELATED APPLICATION

This application is a National Stage application under 35 U.S.C. §371 of PCT/GB03/04019 filed Sep. 17, 2003, which claims priority from GB0221688.5 filed Sep. 18, 2002.

The present invention relates to compositions comprising an oxidized cellulose and a chitosan, and the uses thereof for wound healing.

Oxidized cellulose is produced by the oxidation of cellulose, for example with dinitrogen tetroxide. This process converts primary alcohol groups on the saccharide residues to carboxylic acid group, forming uronic acid residues within the cellulose chain. The oxidation does not proceed with complete selectivity, and as a result hydroxyl groups on carbons 2 and 3 are occasionally converted to the keto form. These ketone units introduce an alkali labile link, which at pH 7 or higher initiates the decomposition of the polymer via formation of a lactone and sugar ring cleavage. As a result, oxidized cellulose is biodegradable and bioabsorbable under physiological conditions.

The preferred oxidized cellulose for practical applications is oxidized regenerated cellulose (ORC) prepared by oxidation of a regenerated cellulose, such as rayon. It has been known for some time that ORC has haemostatic properties. ORC has been available as a haemostatic product called SURGICEL (Registered Trade Mark of Johnson & Johnson Medical, Inc.) since 1950. This product is produced by the oxidation of a knitted rayon material.

A modification of porosity, density and knit pattern led to the launch of a second ORC fabric product, INTERCEED (Registered Trade Mark—Johnson & Johnson Medical, Inc.) which was shown to reduce the extend of post-surgical adhesions in abdominal surgery.

U.S. Pat. No. 2,517,772 (Doub et al.) describes improved haemostatic materials obtained by impregnating ORC fabric with thrombin.

EP-A-0437095 describes a neutralised ORC material prepared by contacting an as-synthesised acidic ORC material with a solution of a basic salt of a weak organic acid, such as sodium acetate. The resulting neutralised product is indicated for haemostasis and adhesion prevention.

EP-A-0562862 describes bioabsorbable sponge materials for use as wound implants. The materials comprise a collagen sponge matrix having an oriented substructure therein. The matrix and/or substructures may comprise oxidised regenerated cellulose. There is no disclosure of the use of such materials for the treatment of chronic wounds.

W098/00180 describes the use of freeze-dried sponges of collagen admixed with oxidized regenerated cellulose (ORC) for the treatment of chronic wounds.

EP-A-0393825 describes absorbent bodies based on mixtures of cellulose fibers and chitosan. WO00/01166 describes non-fibrous porous materials made by freeze drying aqueous mixtures of at least two polysaccharides, which may be selected from chitin/chitosan or their derivatives, calcium/sodium alginates, pectin/pectates, carrageenan, CMC, other derivatives of cellulose, hyaluronic acid, derivatives of starch and/or chondroitin.

The above-described wound dressing materials provide important advantages. The materials are of natural, biological origin (albeit chemically modified), and consequently tend to have low antigenicity. The materials are generally bioabsorbable, which reduces the trauma associated with removal of conventional wound dressing materials from the surface of the wound. Furthermore, some of these materials can have positive therapeutic effects on wound healing.

However, certain difficulties remain. For example, collagen as a component of wound dressings is prone to denaturation when it is sterilized by gamma-irradiation. Collagen is extracted from natural sources and can be antigenic to certain patients unless stringent measures are taken to purify the collagen, which add to its cost.

Therefore, there remains a need for improved wound dressing materials of this general type exhibiting control of physical properties and biological absorption rates, therapeutic effects on wound healing, reduced cost, and reduced antigenic response.

It is an object of the present invention to provide improved wound dressing materials for mammalian wounds, and especially for human, chronic wounds, such as venous ulcers, decubitis ulcers and diabetic ulcers. Such chronic wounds generally exhibit little or no bleeding or adhesion to other body tissues.

Accordingly, in a first aspect the present invention provides a wound dressing composition comprising a chitosan and an oxidized cellulose.

Preferably, the oxidized cellulose comprises oxidized regenerated cellulose (ORC). The oxidized regenerated cellulose (ORC) can be obtained by the process described in U.S. Pat. No. 3,122,479, the entire content of which is incorporated herein by reference. This material offers numerous advantages including the features that it is biocompatible, biodegradable, non-immunogenic and readily commercially available. ORC is available with varying degrees of oxidation and hence rates of degradation. The ORC may be used in the form of insoluble fibers, including woven, non-woven and knitted fabrics. In other embodiments, the ORC is in the form of water-soluble low molecular weight fragments obtained by alkali hydrolysis of ORC.

In preferred embodiments, the oxidized cellulose is in the form of particles, such as fiber particles or powder particles, preferably dispersed in a suitable solid or semisolid topical medicament vehicle. In particular, the materials preferably contain ORC fibers, wherein a volume fraction of at least 80% of the fibers have lengths in the range of 20 µm to 1000 µm. Such a size distribution can be achieved, for example, by milling an ORC cloth, followed by sieving the milled powder to remove fibers outside the range. Preferably, the average (mean by volume) length of the ORC fibers is in the range 250 µm to 450 µm. The selection of ORC fiber lengths in this range results in easy mixing of the ORC and chitosan and highly homogeneous products. The ORC is more thoroughly complexed with the chitosan, which results in enhanced therapeutic properties of the sponge.

Preferably, the oxidised cellulose has an average molecular weight greater than 50,000. Such oxidised cellulose is substantially insoluble in wound fluids, but will undergo very gradual breakdown into bioresorbable fragments at physiological pH. Preferably, the oxidized cellulose is not neutralized. However, the present invention encompasses the use of partially or completely neutralised materials as described in EP-A-0437095 for the preparation of medicaments for the treatment of chronic wounds as hereinbefore defined.

Chitin is a natural biopolymer composed of N-acetyl-D-glucosamine units. Chitin may be extracted from the outer shell of shrimps and crabs in known fashion. The chitin is then partially deacetylated, for example by treatment with 5M-15M NaOH, to produce chitosan. Complete deacetylation of the chitin is not a practical possibility, but preferably the chitosan is at least 50% deacetylated, more preferably at least 75% deacetylated. Chitosan has been employed for wound treatment in various physical forms, e.g. as a solution/gel; film/membrane; sponge; powder or fiber. Chitosan in the free base form is swellable but not substantially soluble in water at near-neutral pH, but soluble in acids due to the presence of ammonium groups on the chitosan chain. The solubility of the chitosan may be reduced by cross-linking, for example with epichlorhydrin. Typically, the average molecular weight of the chitosan as determined by gel permeation chromatography is from about $10^5$ to about $10^6$.

The compositions according to the present invention preferably comprise an intimate mixture of the chitosan and the oxidized cellulose. Preferably, the intimate mixture comprises a mixed solution or dispersion of the chitosan and the oxidized cellulose in a suitable vehicle, such as a solvent, or a solid composition produced by removing solvent from such a solution or dispersion. (By dispersion is meant a distribution of discrete solid particles in the vehicle, e.g. a colloidal dispersion or dispersion formed by shear mixing). Such intimate mixing results in maximum chemical complexation between the amine groups of the chitosan and the carboxylate groups on the oxidized cellulose.

Preferably, the chitosan makes up at least 5%, more preferably at least 10%, 20% or 30% of the composition. Preferably, the Oxidized cellulose also makes up at least 5%, more preferably at least 10%, 20% or 30% of the composition. Preferably, the chitosan and oxidized cellulose together make up at least 25% by weight, more preferably 50% or 75% by weight of the wound dressing material, and in some embodiments at least 90% by weight of the material. In certain preferred embodiments, the material consists essentially of the chitosan and oxidized cellulose.

Other components of the material according to the invention may include 0-25% by weight, for example from about 1 to about 20% by weight, of one or more other biocompatible polysaccharides, for example alginates such as sodium alginate or calcium alginate, starch derivatives such as sodium starch glycolate, cellulose derivatives such as methyl cellulose or carboxymethyl cellulose, or glycosaminoglycans such as hyaluronic acid or its salts, chondroitin sulfate or heparan sulfate. The materials according to the present invention may also comprise up to about 25% by weight, for example from about 1 to about 20% by weight, of one or more structural proteins selected from the group consisting of fibronectin, fibrin, laminin, elastin, collagen and mixtures thereof. Preferably the protein comprises collagen, and more preferably it consists essentially of collagen. The materials according to the present invention may also comprise up to about 20% by weight, preferably from about 2% to about 10% by weight of water. The material according to the present invention may also contain 0-40% by weight, for example from about 5 to about 25% by weight, of a plasticiser, preferably a polyhydric alcohol such as glycerol or sorbitol.

In certain embodiments, the materials according to the present invention may also comprise up to about 10% by weight, for example from about 0.01 to about 5% by weight, typically from about 0.1 to about 2% by weight of one or more therapeutic wound healing agents, such as non-steroidal anti-inflammatory drugs (e.g. acetaminophen), steroids, local anaesthetics, antimicrobial agents, or growth factors (e.g. fibroblast growth factor or platelet derived growth factor). The antimicrobial agent may, for example, comprise an antiseptic, an antibiotic, or mixtures thereof. Preferred antibiotics include tetracycline, penicillins, terramycins, erythromycin, bacitracin, neomycin, polymycin B, mupirocin, clindamycin and mixtures thereof. Preferred antiseptics include silver, including colloidal silver, silver salts including salts of one or more of the anionic polymers making up the material, silver sulfadiazine, chlorhexidine, povidone iodine, triclosan, sucralfate, quaternary ammonium salts and mixtures thereof. These medicated wound dressing materials according to the invention provide sustained release of the therapeutic agents as the wound dressing material breaks down in use.

All of the above percentages are on a dry weight basis.

Preferably, the weight ratio of chitosan to oxidized cellulose is from about 1:99 to about 99:1. More preferably, the weight ratio is in the range about 1:9 to about 9:1, more preferably it is in the range about 4:1 to about 1:4, still more preferably in the range about 2:1 to about 1:2, and most preferably in the ratio chitosan:oxidized cellulose of from about 60:40 to about 50:50. In certain embodiments the material consists essentially of about 55 wt % chitosan and about 45 wt % oxidized cellulose, on a dry weight basis.

The composition according to the present invention may be in any convenient form, such as a powder, microspheres, flakes, a mat or a film.

In certain embodiments, the composition according to the present invention is in the form of a semisolid or gel ointment for topical application.

In certain embodiments, the composition according to the present invention is in the form of a freeze-dried or solvent-dried bioabsorbable sponge for application to a chronic wound. Preferably, the average pore size of the sponge is in the region of 10-500 μm, more preferably about 100-300 μm. A suitable sponge has been made by freeze-drying or solvent drying an aqueous dispersion consisting essentially of chitosan particles or fibers and ORC fibers, together with suitable therapeutic agents.

In yet other embodiments, the composition according to the present invention is in the form of a flexible film, which may be continuous or interrupted (e.g. perforated). The flexible film preferably comprises a plasticiser to render it flexible, such as glycerol.

The ready availability of both chitosan and ORC having a range of controllable properties means that the properties of the compositions the present invention can be controlled to an exceptional degree. In particular, the rate of biological absorption, porosity and density of the materials can be controlled.

In a second aspect the present invention provides a wound dressing comprising a wound dressing composition according to the first aspect of the invention.

The wound dressing is preferably in sheet form and comprises an active layer of the composition according to the invention. The active layer would normally be the wound contacting layer in use, but in some embodiments it could be separated from the wound by a liquid-permeable top sheet. Preferably, the area of the active layer is from about 1 cm$^2$ to about 400 cm$^2$, more preferably from about 4 cm$^2$ to about 100 cm$^2$.

Preferably, the article further comprises a backing sheet extending over the active layer opposite to the wound facing side of the active layer. Preferably, the backing sheet is larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

Preferably, the backing sheet is substantially liquid-impermeable. The backing sheet is preferably semipermeable.

That is to say, the backing sheet is preferably permeable to water vapour, but not permeable to liquid water or wound exudate.

Preferably, the backing sheet is also microorganism-impermeable. Suitable continuous conformable backing sheets will preferably have a moisture vapor transmission rate (MVTR) of the backing sheet alone of 300 to 5000 $g/m^2/24$ hrs, preferably 500 to 2000 $g/m^2/24$ hrs at 37.5° C. at 100% to 10% relative humidity difference. The backing sheet thickness is preferably in the range of 10 to 1000 micrometers, more preferably 100 to 500 micrometers.

The MVTR of the dressing according to the present invention as a whole is lower than that of the backing sheet alone, because the apertured sheet partially obstructs moisture transfer through the dressing. Preferably, the MVTR of the dressing (measured across the island portion of the dressing) is from 20% to 80% of the MVTR of the backing sheet alone, more preferably from 20% to 60% thereof, and most preferably about 40% thereof. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive (where present) layer should be moisture vapor transmitting and/or patterned to allow passage of water vapor therethrough. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is preferably 20 to 250 $g/m^2$, and more preferably 50 to 150 $g/m^2$. Polyurethane-based pressure sensitive adhesives are preferred.

Further layers of a multilayer absorbent article may be built up between the active layer and the protective sheet. For example, these layers may comprise an apertured plastic film to provide support for the active layer in use, in which case the apertures in the film are preferably aligned in register with the apertures in the hydrogel layer.

The dressing may further comprise an absorbent layer between the active layer and the protective sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam prepared in accordance with EP-A-0541391, the entire content of which is expressly incorporated herein by reference. In other embodiments, the absorbent layer may be a nonwoven fibrous web, for example a carded web of viscose staple fibers. The basis weight of the absorbent layer may be in the range of 50-500 $g/m^2$, such as 100-400 $g/m^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25°.

Preferably, the absorbent layer or layers are substantially coextensive with the chitosan/ORC layer.

The wound facing surface of the dressing is preferably protected by a removably cover sheet. The cover sheet is normally formed from flexible thermoplastic material. Suitable materials include polyesters and polyolefins. Preferably, the adhesive-facing surface of the cover sheet is a release surface. That is to say, a surface that is only weakly adherent to the active layer and the adhesive on the backing sheet to assist peeling of the hydrogel layer from the cover sheet. For example, the cover sheet may be formed from a non-adherent plastic such as a fluoropolymer, or it may be provided with a release coating such as a silicone or fluoropolymer release coating.

Preferably, the wound dressing is sterile and packaged in a microorganism-impermeable container.

In a third aspect, the present invention provides the use of a wound dressing composition according to the first aspect of the invention for the preparation of a dressing for the treatment of a wound. Preferably, the wound is a chronic wound, for example a wound selected from the group consisting of venous ulcers, decubitis ulcers and diabetic ulcers.

It has been found that the chitosan/oxidized cellulose compositions according to the first aspect of the present invention have an excellent ability to bind to growth factors, in particular, platelet derived growth factor. Accordingly, the present invention also provides the use of compositions according to the first aspect of the invention to bind one or more cell growth factors. Preferably, the cell growth factor is platelet derived cell growth factor (PDGF).

The present invention further provides a method of separating cell growth factors from a biological sample or organism, the method comprising: contacting the biological sample or organism with a material comprising a compositions according to the first aspect of the invention, the contacting being carried out in vivo or in vitro, to bind the growth factors to the material. Preferably, the method then further comprises recovering the bound growth factors from the material.

The present invention further provides a method of preparing an active wound dressing material comprising the step of:
 (i) contacting a material comprising a compositions according to the first aspect of the invention with a biological medium containing cell growth factors to bind the cell growth factors to the material;
 (ii) washing and drying the material having the cell growth factors bound thereto to form said active wound dressing material. Preferably, the cell growth factors comprise platelet derived growth factor.

In another aspect, the present invention provides a method of treatment of a chronic wound in a mammal, such as a decubitis ulcer, a venous ulcer or a diabetic ulcer. The method comprises applying a dressing according to the second aspect of the invention to the wound.

Preferably, the dressing is applied to the chronic wound for a period of at least 1 hour, more preferably at least 6 hours, and most preferably at least 12 hours. The treatment may be extended for several days or weeks, with dressing changes as appropriate, if necessary for chronic wounds. This contrasts with haemostatic applications of ORC, which typically last only a few seconds or minutes.

Without wishing to the bound by any theory, it is thought that the chitosan/oxidized cellulose compositions promote chronic wound healing in at least some of the following ways. Firstly, the complex binds to growth factors such as PDGF, EGF and FGF to retain these growth factors at the wound site. otherwise, such growth factors tend to be carried away from the wound site along with the wound exudate. The gradual breakdown of chitosan/oxidized cellulose at physiological pH results in gradual release of the growth factors back into the wound. A second reason is that the material is fully bioresorbable and physiologically acceptable. A third reason may be that the oligosaccharide fragments produced by the breakdown of oxidized cellulose and chitosan in vivo themselves promote chronic wound healing.

Preferably, the chronic wound is selected from the group consisting of venous ulcers, decubitis ulcers and diabetic ulcers. Preferably, the chronic wound is substantially or completely non-bleeding. The term "chronic wound" preferably does not encompass a periodontal disorder or disease.

The chitosan/oxidized cellulose complexes used in the present invention can be made by a process comprising the steps of: providing an dispersion of a chitosan in a suitable solvent, preferably an aqueous dispersion; immersing or dispersing oxidized cellulose in the solvent; followed by removing solvent from the dispersion to leave a solid material comprising chitosan complexed with oxidized cellulose.

The oxidized cellulose may be added to the aqueous dispersion of chitosan in the form of a suspension or solution of the oxidized cellulose, preferably at a comparable pH to the chitosan suspension, following by mixing by stirring or homogenisation. Alternatively, dry fibers or fabric of oxidized cellulose may be dispersed or immersed in the aqueous dispersion of chitosan.

The optional, additional components in the materials according to the present invention are preferably included in the dispersion prior to removal of solvent from the dispersion.

Preferably, the pH of the dispersion is preferably adjusted to pH in the range of about 1 to about 10, preferably pH about 2 to about 8. Chitosan is soluble at low pH, which can be desirable for forming certain products such as films. Oxidized cellulose undergoes hydrolysis to soluble fragments at high pH.

The solvent can be removed from the dispersion by evaporation, for example by evaporation from the dispersion in a tray to leave a film of material. In other embodiments the solvent, preferably water, is removed by freeze-drying (lyophilizing) or solvent-drying to produce the material in the form of a sponge. Preferably, the solvent dispersion contains 5-30 mg/ml of chitosan. Preferably, the method of lyophilisation is similar to that described for a collagen-based sponge in U.S. Pat. No. 3,157,524, the entire content of which is incorporated herein by reference.

In certain embodiments the process may further comprise treating the chitosan and/or the oxidized cellulose in the dispersion, or in the dried material, with a cross-linking agent such as epichlorhydrin, carbodiimide, hexamethylene diisocyanate (HMDI) or glutaraldehyde.

Alternatively, cross-linking may be carried out dehydrothermally. The method of cross-linking can markedly affect the final product. For example, HMDI cross-links the primary amino groups on the chitosan within the complex, whereas carbodiimide cross-links carbohydrate on the ORC to primary amino groups on the chitosan.

It will be appreciated that any additional or alternative features that are described above in relation to any one aspect of the invention are also alternative or additional features in relation to any other aspect of the invention, either alone or in combination.

BRIEF DESCRIPTION OF THE SEVERAL VIEWS OF THE DRAWINGS

Specific embodiments of the present invention will now be described further, by way of example, with reference to the accompanying drawings, in which.

Figure 1:
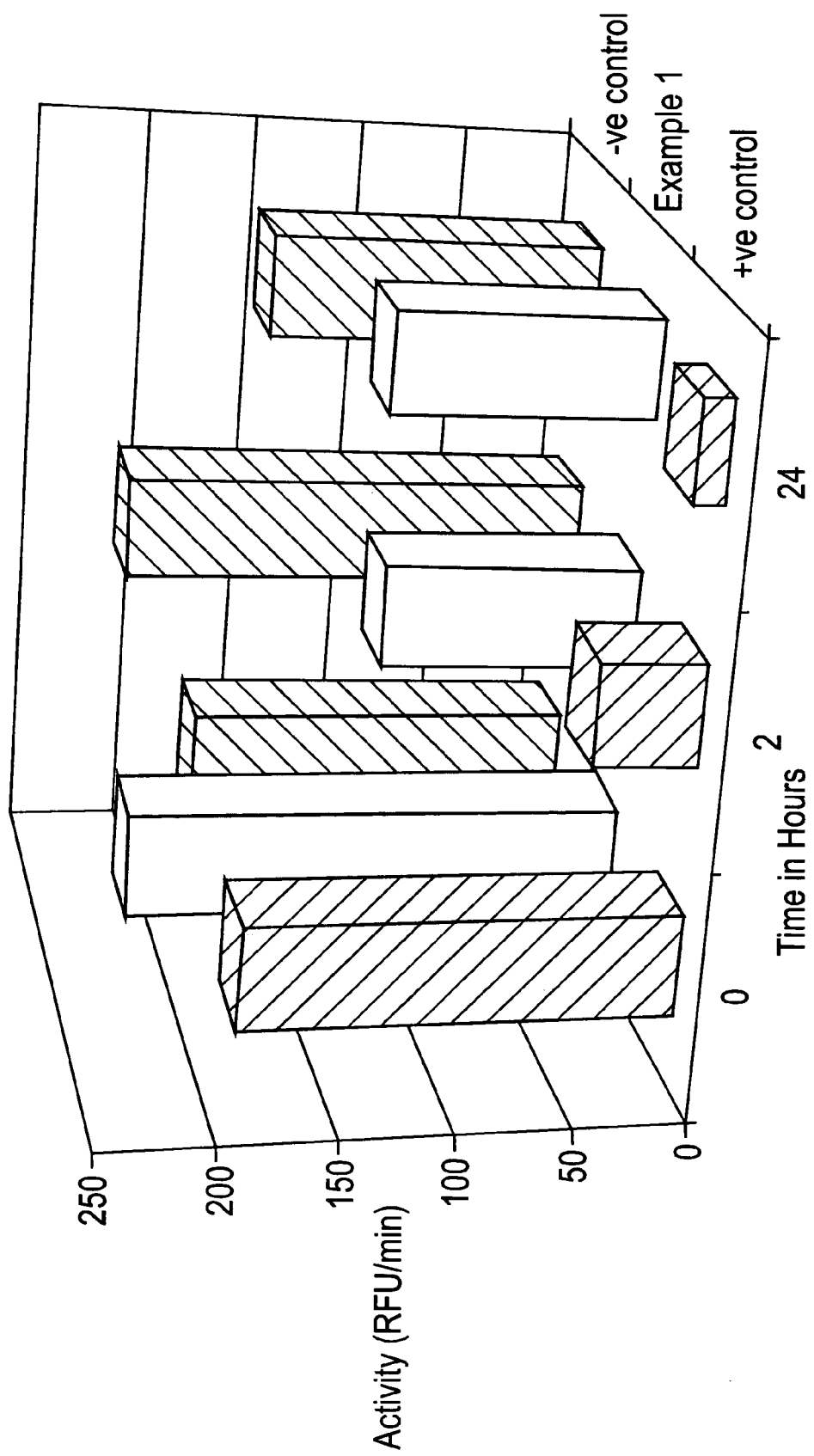
FIG. 1 shows a graph of elastase activity against time for a wound dressing material according to the present invention as compared with positive and negative controls.

Reference Example 1: Preparation of a Collagen/Fibrous ORC Sponge

A freeze-dried collagen/ORC sponge is prepared as follows.

First, the collagen component is prepared from bovine corium as follows. Bovine corium is split from cow hide, scraped and soaked in sodium hypochlorite solution (0.03% w/v) to inhibit microbial activity pending further processing. The corium is then washed with water and treated with a solution containing sodium hydroxide (0.2% w/v) and hydrogen peroxide (0.02% w/v) to swell and sterilize the corium at ambient temperature. The corium splits then undergo an alkali treatment step in a solution containing sodium hydroxide, calcium hydroxide and sodium bicarbonate (0.4% w/v, 0.6% w/v and 0.05% w/v, respectively) at pH greater than 12.2, ambient temperature, and for a time of 10-14 days, with tumbling, until an amide nitrogen level less than 0.24 mmol/g is reached. The corium splits then undergo an acid treatment step with 1% hydrochloric acid at ambient temperature and pH 0.8-1.2. The treatment is continued with tumbling until the corium splits have absorbed sufficient acid to reach a pH less than 2.5. The splits are then washed with water until the pH value of corium splits reaches 3.0-3.4. The corium splits are then comminuted with ice in a bowl chopper first with a coarse comminution and then with a fine comminution setting. The resulting paste, which is made up in a ratio of 650 g of the corium splits to 100 g of water, as ice, is frozen and stored before use in the next stage of the process. However, the collagen is not freeze-dried before admixture with the ORC in the next stage.

The ORC component of the freeze-dried pad is prepared as follows. A SURGICEL cloth (Johnson & Johnson Medical, Arlington) is milled using a rotary knife cutter through a screen-plate, maintaining the temperature below 60° C.

The milled ORC powder and the required weight (according to solids content) of frozen collagen paste are then added to a sufficient amount of water acidified with acetic acid to obtain a pH value of 3.0 and a total solids content of 1.0%. The mixture is homogenized through a Fryma MZ130D homogenizer, progressively diminishing the settings to form a homogeneous slurry. The pH of the slurry is maintained at 2.9-3.1. The slurry temperature is maintained below 20° C., and the solids content is maintained at 1%±0.07.

The resulting slurry is pumped to a degassing vessel. Vacuum is initiated for a minimum of 30 minutes, with intermittent stirring, to degas the slurry. The slurry is then pumped into freeze-drier trays to a depth of 25 mm. The trays are placed onto freezer shelves where the temperature has been preset to −40° C. The freeze-drier programme is then initiated to dry and dehydrothermally cross-link the collagen and ORC to form thick sponge pads. On completion of the cycle, the vacuum is released, the freeze-dried blocks are removed, and are then split to remove the top and bottom surface layers, and to divide the remainder of the blocks into 3 mm-thick pads. The step of splitting the freeze-dried blocks into pads is carried out with a Fecken Kirfel K1 slitter. Finally, the pads are die-cut to the desired size and shape on a die-cutter, packaged, and sterilized with 18-29 KGy of cobalt 60 gamma-irradiation. Surprisingly, this irradiation does not cause significant denaturation of the collagen, which appears to be stabilized by the presence of ORC. The resulting freeze-dried collagen ORC pads have a uniform, white, velvety appearance. The thickness of the pads is 3.2±0.17 mm (N=8 batches). These pads are used as the positive control in the Procedures described below.

Reference Example 2: Preparation of an Alginate/Fibrous ORC Sponge

An alginate/fibrous ORC sponge was prepared as described in Reference Example 1, but with replacement of the collagen by an equal weight fraction of alginate Sodium alginate was obtained from Pronova Biomedical in a powdered form. The powder was dissolved in ice cold water at a concentration of 2% w/v by mixing with a paddle stirrer. The solution was then diluted to 1% solids by the addition of an equal volume of 0.1M acetic acid. A known weight of the sodium alginate solution was then added to the ORC to give a final ratio of 45% ORC/55% sodium alginate in the final material. The sponges were then prepared as in example 1.

Reference Example 3: Preparation of a Hyaluronate/Fibrous ORC Sponge

A hyaluronate/fibrous ORC sponge was prepared as described in Reference Example 1, but with replacement of the collagen by an equal weight fraction of alginate Sodium Hyaluronate with an average molecular weight distribution of 500,000 daltons was obtained from Lifecore Biomedical Inc. in a powdered form. The powder was dissolved in ice cold water at a 2% w/v concentration with mixing overnight. A known weight of the sodium hyaluronate solution was then added to the ORC to give a final ratio of 45% ORC/55% sodium hyaluronate in the final material. The sponges were then prepared as in example 1.

Reference Example 4: Preparation of a Pectin/Fibrous ORC Sponge

A pectin/fibrous ORC sponge was prepared as described in Reference Example 1, but with replacement of the collagen by an equal weight fraction of pectin Apple derived pectin was obtained from the Sigma Chemical Co. The powder was dissolved in ice cold water at 2% w/v with stirring overnight. A known weight of the pectin solution was then added to the ORC to give a final ratio of 45% ORC/55% pectin in the final material. The sponges were then prepared as in example 1.

Reference Example 5: Preparation of a Beta-Glucan/Fibrous ORC Sponge

A beta-glucan/fibrous ORC sponge was prepared as described in Reference Example 1, but with replacement of the collagen by an equal weight fraction of a beta-glucan B-Glucan was obtained in a powdered form from Sigma Chemical Company, and was dissolved in ice cold water at 2% w/v by stirring overnight. The final solution was diluted with an equal volume of 0.1M Acetic acid to give a solution with a final concentration of 1% w/v in 0.05M acetic acid. A known weight of the b-glucan solution was then added to the ORC to give a final ratio of 45% ORC/55% b-glucan in the final material. The sponges were then prepared as in example 1.

Reference Example 6: Preparation of a Locust Bean Gum/Fibrous ORC Sponge

A locust bean gum/fibrous ORC sponge was prepared as described in Reference Example 1, but with replacement of the collagen by an equal weight fraction of locust bean gum Locust Bean Gum was obtained in a granular form from the Sigma Chemical Company. The granules were suspended in ice cold water at 2% w/v. The suspension was then slowly heated to 95° C. to solubilise the gum. The resulting solution was centrifuged at 5000 g to clarify the solution and remove the insoluble fragments of seed coat. The supernatant was then removed and solids content calculated, the solution was then diluted to a final concentration of 1% w/v by the addition of 0.05M acetic acid. A known weight of the locust bean gum solution was then added to the ORC to give a final ratio of 45% ORC/55% locust bean gum in the final material. The sponges were then prepared as in example 1.

EXAMPLE 1: PREPARATION OF A CHITOSAN/FIBROUS ORC SPONGE

A chitosan/fibrous ORC sponge was prepared as described in Reference Example 1, but with replacement of the collagen by an equal weight fraction of a chitosan Chitosan practical grade powder was obtained from the Sigma Chemical Company. The powder was dissolved in ice cold water at a 2% w/v concentration. The solution was then diluted to 1% w/v chitosan by the addition of an equal volume of 0.1M acetic acid. A known weight of the chitosan solution was then added to the ORC to give a final ratio of 45% ORC/55% chitosan in the final material. The sponges were then prepared as in example 1.

EXAMPLE 2: PREPARATION OF A CHITOSAN/ORC FILM

A chitosan/ORC film for application to a wound is made as follows.

15 grams of chitosan powder was mixed in 1.5 liters of water until blended. 2 grams of glycerol were blended into the mixture. 15 grams of ORC fibers prepared as described in Example 1 were then added with high shear mixing. The resulting mixture was then poured into the bottom of a PTFE tray to a thickness of about 5 mm and air-dried to form films of the ORC/chitosan complex.

EXAMPLE 3

A wound treatment gel for topical application to a wound was prepared as follows.

ORC fibers were prepared as described in Example 1 and the resulting fibers are dispersed at 2% w/w concentration in a 3% w/w carboxymethyl cellulose (CMC) aqueous gel containing 2 wt. % of dissolved chitosan chloride.

Procedure I: Binding of Platelet Derived Growth Factor
PDGF binding studies were carried out as follows:

Small sections of test material (approximately 1 cm² squares of INTERCEED® ORC fabric, and approximately 1 cm×0.5 cm×0.4 cm sections of the freeze-dried sponges) were weighed and soaked in 100 mM sodium phosphate dibasic buffer containing 150 mM sodium chloride (total volume 1 ml) for at least one hour at room temperature. Samples were then incubated with 2% bovine serum albumin (BSA) in phosphate buffered saline (PBS) for 2 hours at room temperature. 22 ng of PDGF was then added to each sample in 250 µl of PBS containing 2% BSA, and samples were then incubated for a further hour at 37° C. Each sample was then washed three times with 250 µl PBS, followed by increasing concentrations of sodium chloride. Finally, each sample was washed with 4.0M urea. PDGF ELISA analyses of the original PDGF preparation and the various washings were carried out. The results were as follows:

| Polysaccharide + ORC | Protection of PDGF | Release of PDGF | Comments |
| --- | --- | --- | --- |
| Chitosan | yes | yes | 50% released & retains activity over 96 hr |
| Alginate | ? | no | Since no GF released could not tell if it was protected |
| Hyaluronate | no | yes | 80% released over 96 hr but not active - not protected |
| Pectin | no | yes | 40% released over 96 hr but not active - not protected |
| Beta-glucan | ? | no | Since no GF released could not determine if protected |
| Locust bean gum | ? | no | Since no GF released could not determine if protected |

It can be seen that the chitosan/ORC materials bind PDGF well, and release the bound PDGF with relatively little loss of activity. This is useful for wound healing, since it enables the materials to act as PDGF reservoirs at the wound site, by binding PDGF and then releasing it back into the wound as the material biodegrades in vivo None of the other ORC/polysaccharide complexes studied has this characteristic.

Procedure 2: Elastase Inhibition

The levels of neutrophil-derived elastase present in the wound fluid samples were measured spectrofluorimetrically using substrate activity assays. The substrates comprise short peptides synthesised to mimic the appropriate enzyme cleavage site and contain a fluorescent reporter group which is released upon hydrolysis. Enzyme activity was determined by measuring the rate of production of the fluorimetric compound, 7-amino 4-methyl coumarin. Activity was expressed either as relative fluorescence units per minute (RFU/min) or change in fluorescence when corrected for total protein (RFU/min/mg protein). Each sample was tested times 6 and the average value calculated. The substrate was prepared at a 10 mM-stock concentration, and diluted to a working concentration of 0.5 mM in the appropriate assay buffer. The reaction mixture, combined in a microtiter well (black, flat bottomed) comprised 5 µl wound fluid, 175 µl assay buffer and 20 µl substrate (final concentration 50 µM). The microtiter plate was read immediately at 455 nm (excitation 383 nm) and at timed intervals over the next hour; between readings the plate was covered and incubated at 37° C. Neutrophil-derived elastase-like activity was estimated using the fluorimetric substrate Methoxy-Alanine-Alanine-Proline-Valine 7-amino 4-methyl coumarin (Bachem UK, Ltd.) solubilised in methanol. The assay buffer required for optimal activity of this enzyme was 0.1M Hepes, pH 7.5 containing 0.5M NaCl and 10% dimethyl sulphoxide.

A sample of the collagen/ORC sponge prepared as described in Reference Example 1 was used as a positive control. A sample of SOF-WICK (Registered Trade Mark) gauze was used as a negative control.

The results are shown in FIG. 1. It can be seen that the complex according to the present invention provides a significant inhibition of elastase activity after 2 and 24 hours.

Procedure 3: Collagenase Inhibition

The levels of matrix metalloproteinases present in the wound fluid samples were measured spectrofluorimetrically using substrate activity assays. The substrates comprise short peptides synthesised to mimic the appropriate enzyme cleavage site and contain a fluorescent reporter group which is released upon hydrolysis. Enzyme activity was determined by measuring the rate of production of the fluorimetric compound, 7-amino 4-methyl coumarin. Activity was expressed either as relative fluorescence units per minute (RFU/min) or change in fluorescence when corrected for total protein (RFU/min/mg protein). Each sample was tested times 6 and the average value calculated. The substrate was prepared at a 10 mM-stock concentration, and diluted to a working concentration of 0.5 mM in the appropriate assay buffer. The reaction mixture, combined in a microtiter well (black, flat bottomed) comprised 5 µl wound fluid, 1750 assay buffer and 20 µl substrate (final concentration 50 µM). The microtiter plate was read immediately at 455 nm (excitation 383 nm) and at timed intervals over the next hour; between readings the plate was covered and incubated at 37° C. Matrix metalloproteinase-like activity was estimated utilising the substrate Succinyl-Glycine-Proline-Leucine-Glycine-Proline 7-amino 4-methyl coumarin (Bachem, UK, Ltd.) solubilised in methanol. The assay buffer necessary for maximal MMP activity was 40 mM Tris/HCl, pH 7.4 containing 200 mM NaCl and 10 mM $CaCl_2$.

A sample of the collagen/ORC sponge prepared as described in Reference Example 1 was used as a positive control. A sample of SOF-WICK (Registered Trade Mark) gauze was used as a negative control.

Figure 2:
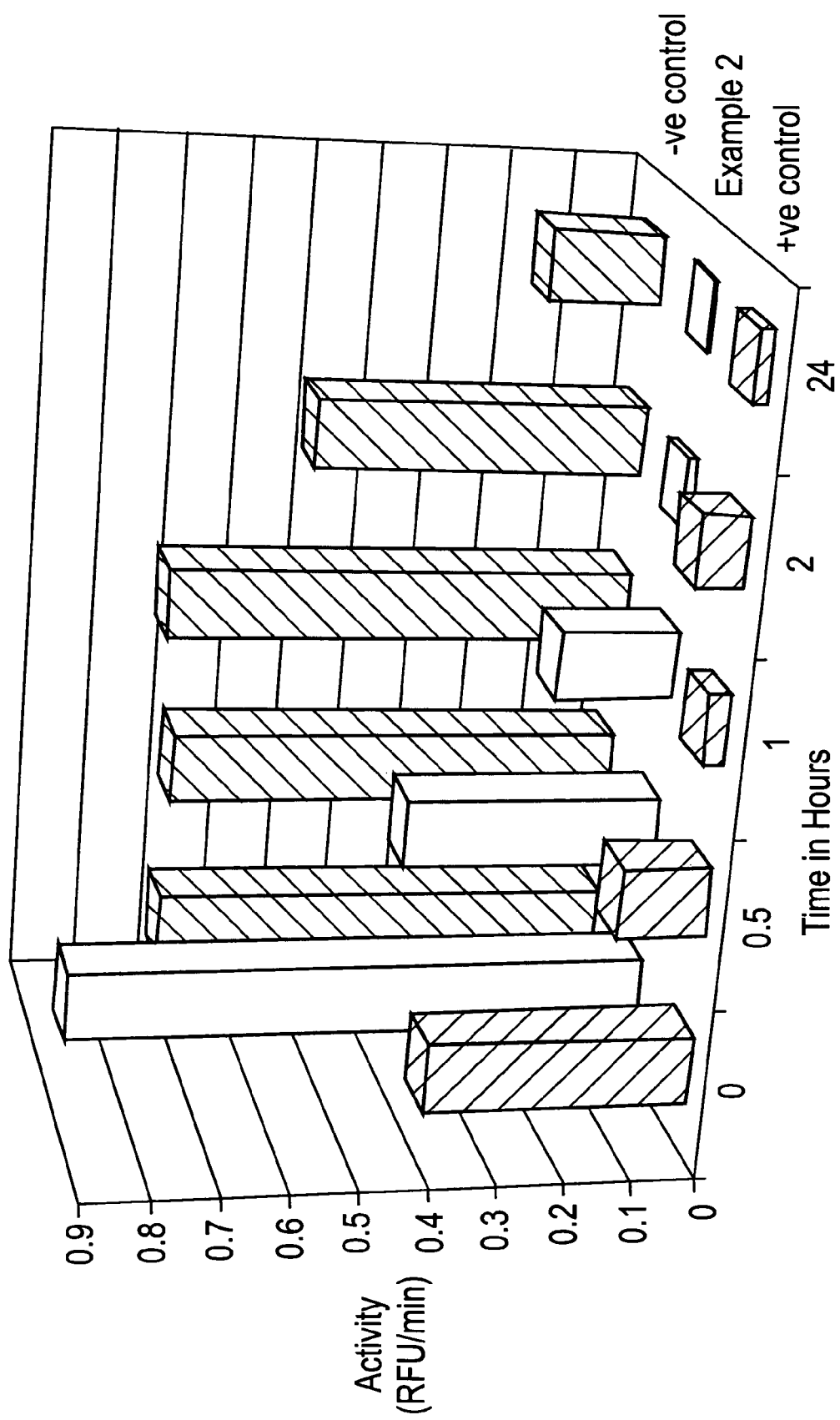
FIG. 2 shows a graph of collagenase activity against time for a wound dressing material according to the present invention as compared with the same positive and negative controls.

The results are shown in FIG. 2. It can be seen that the complex according to the present invention provides rapid inhibition of collagenase activity, and almost complete inhibition after 2 and 24 hours.

The above examples are intended for the purpose of illustration only. Many other embodiments falling within the scope of the accompanying claims will be apparent to the skilled reader.

The invention claimed is:

1. A wound dressing composition comprising an intimate mixture of:
   a chitosan;
   an oxidized regenerated cellulose, wherein the weight ratio of the chitosan to the oxidized regenerated cellulose is in the range of about 2:1 to 1:2; and
   from about 0.01% to about 5% by weight on a dry weight basis of platelet derived growth factor (PDGF);
   wherein the pH of the intimate mixture is in the range of about 2 to 8.

2. A wound dressing composition according to claim 1, wherein said oxidized regenerated cellulose is in the form of dispersed fibers or powder.

3. A wound dressing composition according to claim 1, wherein
   said oxidized regenerated cellulose and chitosan are dispersed in a semi-solid or solid vehicle for topical application.

4. A wound dressing composition according to claim 1, wherein the oxidized regenerated cellulose and chitosan together make up at least 25% by weight of the intimate mixture on a dry weight basis.

5. A wound dressing composition according to claim 4, wherein the oxidized regenerated cellulose and the chitosan together make up at least 50% by weight of the intimate mixture on a dry weight basis.

6. A wound dressing composition according to claim 1, wherein the composition is a flexible film.

7. A wound dressing comprising a wound dressing composition according to claim 1.

8. A wound dressing according to claim 7, which is sterile and packaged in a microorganism-impermeable container.

9. A method of preparing an active wound dressing material comprising the steps of:
   (i) preparing a material comprising a composition according to claim 1; and
   (ii) washing and drying the material to form said active wound dressing material.

10. A wound dressing composition according to claim 1, wherein the pH of the intimate mixture is in the range of about 3 to 7.

\* \* \* \* \*